US 8,058,029 B2

(12) United States Patent
Zhu et al.

(10) Patent No.: US 8,058,029 B2
(45) Date of Patent: *Nov. 15, 2011

(54) **METHOD FOR CLONING AND EXPRESSION OF STUI RESTRICTION ENDONUCLEASE AND STUI METHYLASE IN *E. COLI***

(75) Inventors: Zhenyu Zhu, Beverly, MA (US); Shuang-Yong Xu, Lexington, MA (US)

(73) Assignee: New England Biolabs, Inc., Ipswich, MA (US)

( * ) Notice: Subject to any disclaimer, the term of this patent is extended or adjusted under 35 U.S.C. 154(b) by 392 days.

This patent is subject to a terminal disclaimer.

(21) Appl. No.: 12/279,359

(22) PCT Filed: Feb. 27, 2007

(86) PCT No.: PCT/US2007/005099
§ 371 (c)(1),
(2), (4) Date: Aug. 14, 2008

(87) PCT Pub. No.: WO2007/103061
PCT Pub. Date: Sep. 13, 2007

(65) Prior Publication Data
US 2009/0029418 A1    Jan. 29, 2009

Related U.S. Application Data

(60) Provisional application No. 60/780,148, filed on Mar. 8, 2006.

(51) Int. Cl.
*C12P 21/04*    (2006.01)
*C12N 15/11*    (2006.01)
*C12N 15/00*    (2006.01)
*C12N 1/20*    (2006.01)

(52) U.S. Cl. .................. 435/69.1; 536/23.2; 435/320.1; 435/252.35

(58) Field of Classification Search ........................ None
See application file for complete search history.

(56) References Cited

U.S. PATENT DOCUMENTS 6,833,447 B1 * 12/2004 Goldman et al. ............ 536/23.1

FOREIGN PATENT DOCUMENTS

WO    WO2007097778    *    8/2007

OTHER PUBLICATIONS

TC1600 Memo (2005).*
Rebase®, <http://rebase.neb.com/rebase> (Apr. 11, 2008).
New England Biolabs catalog 2002-2003 (pp. 61 and 230).
Shimotsu, et al. Gene, 11(3-4):219-225 (1980).
Roberts, et al., Nucleic Acids Res, 33:D230-232 (2005).

* cited by examiner

*Primary Examiner* — Scott Long
(74) *Attorney, Agent, or Firm* — New England Biolabs, Inc; Harriet M. Strimpel

(57) ABSTRACT

The present invention relates to compositions including: (1) isolated DNA encoding the StuI restriction endonuclease and isolated DNA encoding cognate and non-cognate methylase; (2) vectors and cells containing the isolated DNA; and (3) methods for producing the StuI restriction endonuclease.

8 Claims, 5 Drawing Sheets

*stuIR*: StuI endonuclease gene
*stuIM*: StuI methylase gene

Figure 2 - SEQ ID NO:3 (DNA) and SEQ ID NO:4 (protein)

```
   1 GTGACGGTCGAAGTGCCGCAACGTACCAGCCTGGAGTCAAACTTTCCGGCAGCGATGCTT   60
     M  T  V  E  V  P  Q  R  T  S  L  E  S  N  F  P  A  A  M  L
  61 AGTGGCGTCGGCACGAAGGAATCCTGGCGCAAGGAAGTCCACCGCCCAGCCACCAGCACG  120
     S  G  V  G  T  K  E  S  W  R  K  E  V  H  R  P  A  T  S  T
 121 CACAAGTGGTGGGCGAAGCGCCTCGGCACCGTATTTCGGGGGATCATTACGTCGGCGACG  180
     H  K  W  W  A  K  R  L  G  T  V  F  R  G  I  I  T  S  A  T
 181 ACGCCCGATGGAGCCGATGCTGTGGGAGCCTACGGATCGTCGCTCGATCTGGCGGGAGCC  240
     T  P  D  G  A  D  A  V  G  A  Y  G  S  S  L  D  L  A  G  A
 241 ATTGTGCTCGACCCGTTCTCTGGCTCGGGTGTGACCGGCGTGGAAGCCCTCAAACTCGGG  300
     I  V  L  D  P  F  S  G  S  G  V  T  G  V  E  A  L  K  L  G
 301 GCTAAGGCTGTTTGTTTCGACATCAACCCTGTGGCAACGCTCGTTCAGCGTCAAGCTGTT  360
     A  K  A  V  C  F  D  I  N  P  V  A  T  L  V  Q  R  Q  A  V
 361 CAACCGTGGGACCTCGGGTCTCTTGAAGCTGCCTACAAAGAGGTCGAGTCGGCCTGTCGG  420
     Q  P  W  D  L  G  S  L  E  A  A  Y  K  E  V  E  S  A  C  R
 421 TCAGAGGTTGATCGACTCCACCGTACAGAGGACGGGAGGACTGTTCTCTACTACTTCTGG  480
     S  E  V  D  R  L  H  R  T  E  D  G  R  T  V  L  Y  Y  F  W
 481 GTCGCGACCCTCGGGTGCCCCGAGTGCTCCAAAGAAGTTCGCTTGTTCGACTCGCCAGTG  540
     V  A  T  L  G  C  P  E  C  S  K  E  V  R  L  F  D  S  P  V
 541 TTCTCTAAGAACGCTTACCCGAAGCGAGTACCCAAAGCCCAAATTGTCTGTCCCGAGTGC  600
     F  S  K  N  A  Y  P  K  R  V  P  K  A  Q  I  V  C  P  E  C
 601 CTCTCCGTTAAGGAGAGTCGGTATGACTTCGTCACGGAGACGTGTTTGAAGGGCCACGTC  660
     L  S  V  K  E  S  R  Y  D  F  V  T  E  T  C  L  K  G  H  V
 661 ATTACGCAGCGCGGTGCAGCGCGGGGTCAGTTGGCGACATGCGGGAACGGTCACAGCTTC  720
     I  T  Q  R  G  A  A  R  G  Q  L  A  T  C  G  N  G  H  S  F
 721 AAGGTCCTCGGCGCCCTGAACGGGTCGCCACCGGTATACGAGATGTATGCCAAGATGGTG  780
     K  V  L  G  A  L  N  G  S  P  P  V  Y  E  M  Y  A  K  M  V
 781 GCCAACTCGGACGGGTCGAAGAGCTACGAAGCCATCACCGACTGGGACAGGGAACTCTAC  840
     A  N  S  D  G  S  K  S  Y  E  A  I  T  D  W  D  R  E  L  Y
 841 GACGAGTGCGTTGCAGCGCTCGCAGGGCTATCGCAGTCTGCCGTGCTTCCACGCGGTCGG  900
     D  E  C  V  A  A  L  A  G  L  S  Q  S  A  V  L  P  R  G  R
 901 CTTGCTCCCGGCAATAATACTGACCAGGCTCTGAAGTGGAATTTTCGGGAATGGCGCGAA  960
     L  A  P  G  N  N  T  D  Q  A  L  K  W  N  F  R  E  W  R  E
 961 TTCTTCAACGCGCGCCAGCTGGTTTCCCTCTCGCTGATGGCGACGGCGATCCGTGACCTG 1020
     F  F  N  A  R  Q  L  V  S  L  S  L  M  A  T  A  I  R  D  L
1021 ACTGGATCGCCTGAACGCGAAGCGCTTTGTGCCCTGTTTTCAGGAACGCTTGAGTTCAAT 1080
     T  G  S  P  E  R  E  A  L  C  A  L  F  S  G  T  L  E  F  N
1081 AACCTGTTCACATCGTTCAAAGGCGAGGGGACGGGGGCTGTCCGGCATATGTTCAGTCAT 1140
     N  L  F  T  S  F  K  G  E  G  T  G  A  V  R  H  M  F  S  H
1141 CACATCCTCACGCCGGAGCGGACTCCACTGGAGGCGCACCCCTGGGGACGTCGCAGTCCT 1200
     H  I  L  T  P  E  R  T  P  L  E  A  H  P  W  G  R  R  S  P
1201 CCGGTGCGTTCTCCACTCTCTTCAAGAGTCGTCTGCAGCGTGCTCACGAGTACAAGACGA 1260
     P  V  R  S  P  L  S  S  R  V  V  C  S  V  L  T  S  T  R  R
1261 AACCTGCAGACCTCGTTGACCGGGGTGCAGGGATCGAGCGGATCTCCGGAGTGTCAAAGC 1320
     N  L  Q  T  S  L  T  G  V  Q  G  S  S  G  S  P  E  C  Q  S
1321 CAGTGGGCGCGAGCATTGCGGACTCATGGGAGTCTTTCGTCTCGATCGAAGGGCAGGCGG 1380
     Q  W  A  R  A  L  R  T  H  G  S  L  S  S  R  K  G  R  R
1381 CCTATGTCGCCACCAGAAACTCGGCACAGACGGATATTCCGGATGGGTCGGTTGACCTAG 1440
     P  M  S  P  P  E  T  R  H  R  R  I  F  R  M  G  R  L  T  *
```

Figure 3 - SEQ ID NO:1 (DNA) and SEQ ID NO:2 (protein)

```
     GTGTCAGTGAGTGCGGTCGAACAGGTATTTTTGGAATGCGAGCGCGCTCGGGCAGACGGT
  1  ----------+----------+----------+----------+----------+----------+  60
      M  S  V  S  A  V  E  Q  V  F  L  E  C  E  R  A  R  A  D  G
     GACTTGATTCAGCGGGTCTCCGCCAGTGATAAGGAGTACCACTTTCAGAATTGGGTGCAG
 61  ----------+----------+----------+----------+----------+----------+  120
      D  L  I  Q  R  V  S  A  S  D  K  E  Y  H  F  Q  N  W  V  Q
     GCCCGCATAGAGGCATGCAGGCTTTCGTACGATGATCCTGGCCGGAACACCTATCCGGAC
121  ----------+----------+----------+----------+----------+----------+  180
      A  R  I  E  A  C  R  L  S  Y  D  D  P  G  R  N  T  Y  P  D
     TTCCGGCTCATCCATCACCCGGAAGGGTATGAGGTCAAGGGCCTGGAGTTTCCCGGCCGC
181  ----------+----------+----------+----------+----------+----------+  240
      F  R  L  I  H  H  P  E  G  Y  E  V  K  G  L  E  F  P  G  R
     GAGGCGGACTACGACTCAAACTCCCAGGTGCCCACCGGTAACCACGGCGGCCGTGAGGTC
241  ----------+----------+----------+----------+----------+----------+  300
      E  A  D  Y  D  S  N  S  Q  V  P  T  G  N  H  G  G  R  E  V
     TTCTACGTGTTCGGTCGCTACCCGAAGGCAGAGCGCGGCGTCGATGAGTATCCAGTTGTA
301  ----------+----------+----------+----------+----------+----------+  360
      F  Y  V  F  G  R  Y  P  K  A  E  R  G  V  D  E  Y  P  V  V
     GATCTGGTGGTGTGCCACGGCAGCTTCCTCAATGCCGATAGTGAGTACGTTCATAAGAAC
361  ----------+----------+----------+----------+----------+----------+  420
      D  L  V  V  C  H  G  S  F  L  N  A  D  S  E  Y  V  H  K  N
     AAGTCGTTCCGTGGCTTTGGCTCGTACGGAGACATCCTGGTCCGCGACCGCAAAATGTAC
421  ----------+----------+----------+----------+----------+----------+  480
      K  S  F  R  G  F  G  S  Y  G  D  I  L  V  R  D  R  K  M  Y
     GTCGTGCCAACGCCGTTCGCACTAGCTTCCGGAACCGCAGGGCTCGCGACCCTGATCGTG
481  ----------+----------+----------+----------+----------+----------+  540
      V  V  P  T  P  F  A  L  A  S  G  T  A  G  L  A  T  L  I  V
     CCTACTGAATTCGAGCCACAGTCGGATACTCTCGTTCAGGTGGGTGAACTTGATCGGACC
541  ----------+----------+----------+----------+----------+----------+  600
      P  T  E  F  E  P  Q  S  D  T  L  V  Q  V  G  E  L  D  R  T
     GAGGTTGACGAGGTCATCGTGTCGTACGAGTTCAACCTTCAGACAAATGAGATGGTGACG
601  ----------+----------+----------+----------+----------+----------+  660
      E  V  D  E  V  I  V  S  Y  E  F  N  L  Q  T  N  E  M  V  T
     CATAAGGCGCCGAATCTCAATGCAGGTAAGGTCCACAGTTTCCGAGCATATCGCTCGCGC
661  ----------+----------+----------+----------+----------+----------+  720
      H  K  A  P  N  L  N  A  G  K  V  H  S  F  R  A  Y  R  S  R
     GGTGCGGGCGATTCTAAGCCGGTTTCCCTCGCAGGGGGTCGGCTGTGA
721  ----------+----------+----------+----------  768
      G  A  G  D  S  K  P  V  S  L  A  G  G  R  L  *
```

METHOD FOR CLONING AND EXPRESSION OF STUI RESTRICTION ENDONUCLEASE AND STUI METHYLASE IN *E. COLI*

CROSS REFERENCE

This application is a §371 application of international application number PCT/US2007/005099 filed on Feb. 27, 2007, which claims priority from U.S. provisional application No. 60/780,148 filed on Mar. 8, 2006, herein incorporated by reference.

BACKGROUND OF THE INVENTION

Restriction endonucleases are enzymes that occur naturally in certain unicellular microbes—mainly bacteria and archaea—and that function to protect these organisms from infections by viruses and other parasitic DNA elements. Restriction endonucleases bind to specific sequences of nucleotides ('recognition sequence') in double-stranded DNA molecules (dsDNA) and cleave the DNA, usually within or close to the sequence, generating DNA fragments of various sizes. In vivo, the restriction fragments in turn serves as the substrates for further exonuclease digestion, leading to total degradation. Restriction endonucleases commonly occur with one or more companion enzymes termed modification methyltransferases. Methyltransferases bind to the same sequences in dsDNA as the restriction endonucleases they accompany, but instead of cleaving the DNA, they alter it by the addition of a methyl group to one of the bases within the sequence. This methylation ('modification') prevents the restriction endonuclease from binding to the cleavage sequence, rendering the site resistant to cleavage. Methyltransferases function as cellular antidotes to the restriction endonucleases they accompany, protecting the cell's own DNA from destruction by its restriction endonucleases. Together, a restriction endonuclease and its companion (cognate) modification methyltransferase(s) form a restriction-modification (R-M) system.

A large and varied number of restriction endonucleases have been classified as 'Type II' restriction endonucleases. These enzymes cleave DNA at defined positions, and in purified form can be used to cut DNA molecules into precise fragments for gene cloning and analysis. The biochemical precision of Type II restriction endonucleases exceeds anything achievable by chemical methods, making these enzymes the reagents sine qua non of molecular biology laboratories. In this capacity, as molecular tools for gene dissection, Type II restriction endonucleases have had a profound impact on the life sciences in the past 33 years, transforming the academic and commercial arenas, alike. Their utility has spurred a continuous search for new restriction endonucleases, and a large number have been found. Today more than 221 Type II endonucleases specificities are known, each possessing different DNA cleavage characteristics (Roberts, et al. Nucl. Acids Res. 33:D230-D232 (2005)). (REBASE®, rebase.neb.com/rebase). Concomitantly, the production and purification of these enzymes has been improved by the cloning and over-expression of the genes that encode them in non-natural production strain host cells such as *E. coli*.

Since the various restriction enzymes appear to perform similar biological roles, in much the same ways, it might be thought that they would resemble one another closely in amino acid sequence and behavior. Experience shows this not to be true, however. Surprisingly, far from resembling one another, most Type II restriction enzymes appear unique, resembling neither other restriction enzymes nor any other known kind of protein. Type II restriction endonucleases seem to have arisen independently of one another for the most part during evolution, and to have done so hundreds of times, so that today's enzymes represent a heterogeneous collection rather than a discrete family. Some restriction endonucleases act as homodimers, some as monomers, others as heterodimers. Some bind symmetric sequences, others asymmetric sequences; some bind continuous sequences, others discontinuous sequences; some bind unique sequences, others multiple sequences. Some are accompanied by a single methyltransferase, others by two, and yet others by none at all. When two methyltransferases are present, sometimes they are separate proteins, at other times they are fused. The orders and orientations of restriction and modification genes vary, with all possible organizations occurring. Several kinds of methyltransferases exist, some methylating adenines (m6A-MTases), others methylating cytosines at the N-4 position (m4C-MTases), or at the 5 position (m5C-MTases). Usually there is no way of predicting, a priori, which modifications will block a particular restriction endonuclease, which kind(s) of methyltransferases(s) will accompany that restriction endonuclease in any specific instance, nor what their gene orders or orientations will be.

Great variability exists among restriction-modification systems. Each enzyme is unique in amino acid sequence and catalytic behavior; each occurs in unique enzymatic association, adapted to unique microbial circumstances; and each presents the experimenter with a unique challenge. Sometimes a restriction endonuclease can be cloned and overexpressed in a straightforward manner but more often than not it cannot, and what works well for one enzyme can work not at all for the next. Success with one enzyme is not a predictor of success with another.

SUMMARY OF THE INVENTION

In an embodiment of the invention, an isolated polynucleotide encoding a restriction endonuclease is provided that is capable of recognizing AGGCCT, and includes a polynucleotide sequence having at least 65% sequence identity with SEQ ID NO:1 wherein the restriction endonuclease has at least 50% sequence identity with SEQ ID NO:2. In an additional embodiment, the polynucleotide sequence has at least 75% sequence identity with SEQ ID NO:1 and the restriction endonuclease has at least 60% sequence identity with SEQ ID NO:2. In an additional embodiment of the invention, the polynucleotide sequence has at least 90% sequence identity with SEQ ID NO:1 and the restriction endonuclease has at least 70% sequence identity with SEQ ID NO:2. Additionally, a vector is provided that contains an isolated polynucleotide that encodes a restriction endonuclease as described above. Additionally, a host cell is provided that has been transformed with the vector.

In a further embodiment of the invention, a polynucleotide segment encoding a methylase is provided that is capable of methylating one or more nucleotides in a polynucleotide sequence recognized by the StuI restriction endonuclease, the polynucleotide segment having at least 65% sequence identity with SEQ ID NO:3 wherein the methylase has at least 50% sequence identity with SEQ ID NO:4. In an additional embodiment, the polynucleotide segment has at least 75% sequence identity with SEQ ID NO:1 and the methylase has at least 60% sequence identity with SEQ ID NO:2. In an additional embodiment of the invention, the polynucleotide segment has at least 90% sequence identity with SEQ ID NO:1 and the methylase has at least 70% sequence identity with SEQ ID NO:2. Additionally, a vector is provided that contains the polynucleotide segment encoding a methylase as described above. Additionally, a host cell is provided that has been transformed with the vector.

In a further embodiment of the invention, a polynucleotide segment is provided that encodes a StuI methylase.

In a further embodiment, a method is provided of producing a recombinant StuI restriction endonuclease that includes culturing a host cell transformed with a vector that contains a polynucleotide encoding a restriction endonuclease as described above under conditions suitable for expression of the endonuclease.

BRIEF DESCRIPTION OF THE DRAWINGS

FIG. 2. stuIM, 1440 bp (SEQ ID NO:3) and the encoded stuIM amino acid sequence (SEQ ID NO:4).

FIG. 3. stuIR, 768 bp (SEQ ID NO:1) and the encoded StuRI amino acid sequence (SEQ ID NO:2).

DETAILED DESCRIPTION OF THE INVENTION

Present embodiments of the invention relate to recombinant DNA that encodes StuIR and stuIM, and to the expression of the StuIR in *E. coli* cells that contain the recombinant DNA.

StuIRs and stuIMs are enzymes that are produced by the bacterium *Streptomyces tubercidicus* (Shimotsu et al. *Gene* 11:219-225 (1980)). StuIR binds to the symmetric nucleotide (nt) sequence 5'-AGGCCT-3' in dsDNA moleculesand cleaves the DNA between the G and C in each strand thus: 5'-AGG/CCT-3', producing DNA fragments with blunt ends (/ indicates the position of strand-cleavage). Many restriction endonucleases that occur in nature are accompanied by protective modification methyltransferases. The stuIM gene was the first cloning target in the identification and sequencing of the stuIR.

Hurdles in Cloning R-M System (a) Unsuccessful Methylase Gene Selection

The methylase selection method described in U.S. Pat. No. 5,200,333 is the preferred first approach for cloning restriction-modification systems. It was concluded that there was a stuIM because the genomic DNA from *Streptomyces tubercidicus* is resistant to the StuIR digestion. However, the cloning of stuIM was problematic. Firstly, methylase selection was unsuccessful. Possible reasons for this failure include:
 cleavage within the stuIM gene by the restriction enzymes used to construct the initial libraries;
 failure to clone the proper DNA fragment from the libraries due to the large size of the DNA fragment;
 low expression of the stuIM gene in *E. coli;*
 poor modification of StuIR cleavage sites on a plasmid;
 stuIR gene toxicity resulting from relative over-expression of the stuIR gene as compared with the expression of the stuIM gene when both genes are cloned in the same DNA fragment.

Secondly, protein sequencing of the N-terminus of the StuIR also failed due to the small amount of purified protein and blocked N-terminus on the protein.

(b) Increasing Methylase Gene Selection Pressure

Figure 1:
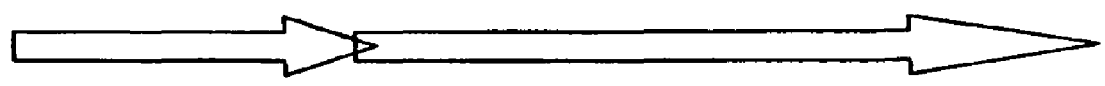
FIG. 1. Gene organization of the StuI R-M system: StuI restriction endonuclease gene (stuIR); StuI methylase gene (stuIM).
Figure 4:
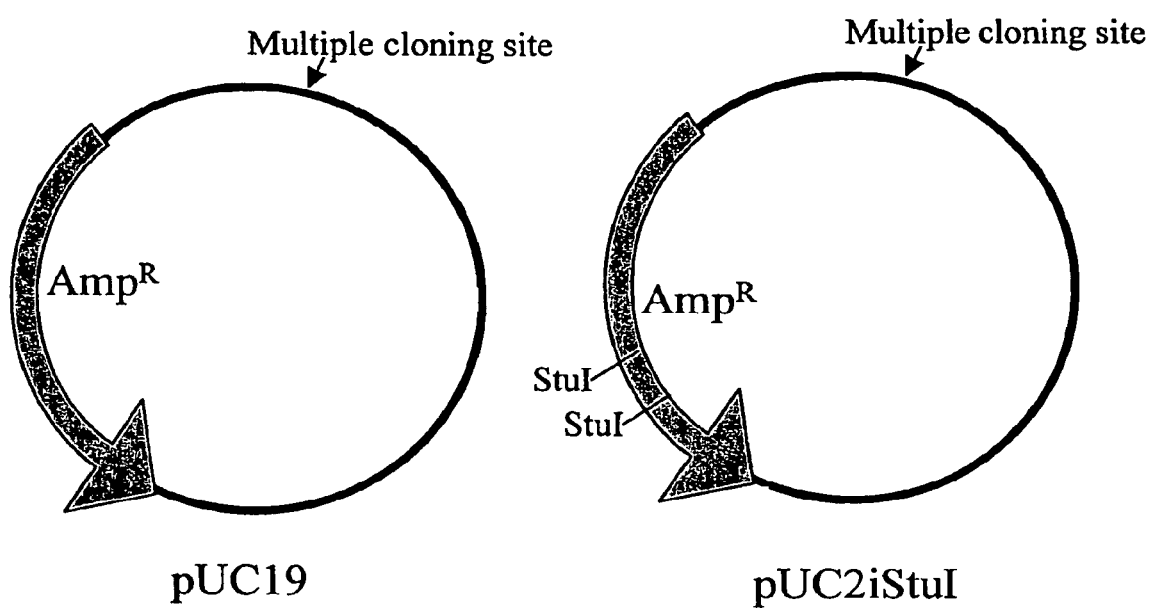
FIG. 4. A map of cloning vector pUC2iStuI that contains two StuI sites.

To increase the chance to discover the gene encoding stuIM, two StuIR cleavage sites (AGGCCT) were engineered into the β-lactamase (bla) gene (Ampicillin-resistant gene) in the plasmid pUC19, generating the plasmid pUC2iStuI (FIG. 4). In the absence of modification by stuIM, the plasmid would not survive the StuIR challenge and selection on Amp plates. Consequently, the presence of the stuIM gene in the plasmid could be selected from the challenged genomic DNA libraries.

A series of libraries were constructed:

(i) NlaIII and Sau3AI partially digested *Streptomyces tubercidicus* genomic DNA were cloned into pUC2iStuI to form a plasmid library containing overlapping fragments of genomic DNA. The plasmid library was transformed into XL10 cells (Stratagene, La Jolla, Calif.). All colonies were pooled and the plasmid DNA was extracted and challenged with StuIR to determine whether modification of the StuIR cleavage site had occurred. If plasmids containing partially digested genomic DNA expressed StuIR, the transformed cells would not survive. Only those cells containing plasmids expressing stuIM or non-endonuclease encoding DNA would be expected to survive, and of these, theoretically only those cells containing the stuIM gene would contain supercoiled plasmids. However, the background of linearized plasmid was very high and it was not possible to recover plasmids encoding stuIM.

(ii) The plasmid DNA was transformed into Rosetta 2 strain (Rosetta 2 strain carries a plasmid with rare tRNA genes) from EMD Biosciences (Damstadt, Germany) as a means to enhance expression of a putative stuIM gene. The plasmid pooled from the Rosetta 2 strain was challenged with StuIR and re-introduced back into the Rosetta 2 strain. A total of 6 colonies were found on the plate. Small cell cultures were made for all 6 transformants and cultured at 37° C. for over 20 h in a shaker. Only one clone that was totally resistant to StuIR was recovered. Plasmid (pST2) extracted from one culture (#2) was totally resistant to the StuIR digestion.

(iii) To examine whether the Rosetta 2 strain was required for stuIM expression, the plasmid pST2 was transformed into other *E. coli* strains: ER2502, ER2683, ER2566, ER2523, and BL21 with or without the resident plasmid encoding rare tRNA genes. As a control, the pST2 plasmid was also transferred into the original Rosetta 2 strain. However, none of the transformants produced plasmids fully resistant to StuIR digestion. The plasmids were isolated from log-phase cells or cells after prolonged incubation (>20 h). While it was possible to obtain the sequence of the stuIM-containing clone as described below, this clone was insufficient for use in cloning a putative restriction endonuclease as it would not protect the host cell from toxicity.

The stuIM gene in the insert of pST2 plasmid was sequenced by primer walking. One open reading frame (ORF) was identified and found to be similar to N6A-methylase genes by BLASTX searches in GenBank. By inverse PCR walking from the stuIM sequence, one ORF adjacent to the methylase gene was found to be different from all known genes. This ORF was the candidate gene for StuIR (FIG. 3).

(c) Insufficient Protection by stuIM to Permit Cloning of stuIR Gene

The stuIM was amplified by PCR from plasmid pST2 inserted into pACYC184. The pACYC184 was transformed into *E. coli* ER2683 (New England Biolabs, Inc. (NEB), Ipswich, Mass.). Six out of nineteen plasmids contained the right size insert by appropriate enzyme digestion. Since there was no StuIR site on the pACYC184 or in the stuIM, the genomic DNA from these strains were extracted and digested with StuIR. None of them were resistant to StuIR digestion. The stuIM expressed from the high-copy-number plasmid did not fully modify the host DNA.

In order to clone StuIR in *E. coli*, it was necessary to overcome the problems associated with incomplete modification by stuIM. Non-cognate methylases was tested to determine whether protection against StuIR cleavage could be achieved. The recognition site of StuIR is AGGCCT. Methylases exist that modify the internal sequence of the StuIR cleavage site to protect DNA from StuIR digestion. After surveying known methylases, HaeIII methylase ($GG^{m5}CC$) (Slatko et al. *Gene* 74:45-50 (1998), FnuDI methylase (U.S. Pat. No. 4,988,620) (GGCC, modification site unknown, 5mC methylation type), and PhoI methylase (GGCC, modification site unknown, N4mC methylation type) genes were selected and were subsequently expressed in *E. coli*. The genomic DNAs from three strains were digested with StuIR. The genomic DNA from two strains with M.HaeIII and M.FnuDI were resistant to StuIR digestion. The M.FnuDI expressed from pACYC-fnuDIM was chosen to pre-modify ER2683 host DNA for expression of the putative stuIR gene.

The ORF adjacent to the stuIM was amplified in PCR and cloned into pUC19. The ligated plasmid was transformed into ER2683 pre-modified with pACYC-fnuDIM. Colonies were picked and grown in LB with Amp and Chloramphenical (Cam) in 4 ml culture overnight. The whole cell culture from 38 samples was tested for endonuclease activity on lambda DNA. Sixteen out of 38 cultures had high StuIR activity. This ORF was thus confirmed to be the stuIR gene. The insert in three clones (#6, #7 and #15) was sequenced. #6 and #15 were confirmed to be the wild-type stuIR gene. The strain was then tested for stability in large cultures and found to be stable. The recombinant StuIR was over-expressed at the level of $5 \times 10^6$ units per gram of wet cells.

In summary, an expression strategy was ultimately developed which overcame a number of hurdles and ultimately proved successful in yielding a StuIR over-expression clone. This strategy relied on the expression of M.FnuDI to protect host DNA against StuI digestion.

The method described herein by which the stuIM and stuIR genes can be cloned and expressed in *E. coli* include one or more of the following steps. The steps are described in more detail in the examples.

(1) Preparation of Genomic DNA and Construction of StuI Genomic DNA Library

Genomic DNA was prepared from *Streptomyces tubercidicus* by the method of general Phenol-Chloroform extraction and freeze-thaw cycles.

Genomic DNA was then partially digested by ApoI, NlaIII, and Sau3AI. Only NlaIII and Sau3AI digestion produced good distribution of DNA fragment sizes ranging from 1.5 to 10 kb. Partially digested genomic DNA preparations were ligated to SphI and BamHI digested, CIP-treated pUC19 vector into which two StuI sites (pUC2iStuI) had been previously engineered in the bla gene, respectively. The ligated DNA mixtures were used to transform XL-10 cells (Stratagene, La Jolla, Calif.). Transformants of two libraries were pooled and plasmid DNA was extracted. The plasmid DNA was transferred into Rosetta 2 strain. The plasmid DNA from Rosetta 2 was prepared to generate primary plasmid libraries.

(2) stuIM Methylase Selection

The primary plasmid libraries were challenged by digestion with StuIR. These DNA digests were then transformed back into *E. Coli* Rosetta 2. Only 6 survivor colonies were found in transformation after StuIR challenge. Plasmids from these 6 colonies were extracted. StuIR-digestion of these plasmids indicated that one clone (#2) (pST2) was resistant to digestion.

Primer walking was carried out to sequence the insert in pST2 plasmid. The insert was flanked by NlaIII, which was ligated to the SphI site of pUC2iStuI. The insert was at least 4 kb with small gaps between the sequenced regions. An ORF of 1440 bp from the 5' half was found to be highly homologous to adenine-specific DNA methylases by NCBI translated BLASTX search (FIG. 2). Since other ORFs in this insert are homologous to other known proteins, and over-expression of the 1440-bp ORF rendered the plasmid resistant to stuIM digestion, this ORF was named stuIM gene.

(3) Inverse PCR Amplification of DNA Upstream of the 5' End of stuIM Gene

No endonuclease activity was found in the cell extracts of the Rosetta 2 strain carrying plasmid pST2. The downstream sequence of the stuIM gene covers ~1724 bp and encodes homologs of transcriptional regulator and caax amino terminal protease family protein. So it was unlikely that the endonuclease gene was located in the downstream sequence. The upstream sequence of the stuIM gene is unique and has no homology to any known genes. Therefore, efforts were concentrated on the extension of more upstream sequence. The DNA sequence was further extended by inverse PCR and direct sequencing of the inverse PCR products. Genomic DNA was first digested with individual restriction enzymes and self-ligated. The resulting circular DNA molecules were used as templates for inverse PCR. The DNA sequence at the 5' end of the stuIM gene was used to design primers for the inverse PCR of chromosomal DNA fragments. The templates from BsrFI, EcoRI, HaeII, HpyCH4IV, KasI, NruI and Tsp509I generated PCR products in inverse PCR. These PCR fragments were purified by spin column and sequenced by the inverse PCR primers.

The template from EcoRI digestion and self-ligation produced 983 bp of additional sequence to the original template, revealing a complete ORF of 768 bp. This gene has no homology to any known genes. It was the candidate gene for stuIR (FIG. 3).

(4) Expression of stuIM Gene in *E. coli*

The expression of a methylase gene was crucial for co-expression of the endonuclease gene. To check the expression of stuIM in different *E. coli* strains, the plasmid pST2 was transformed into the following strains: ER2502, ER2683, ER2566, ER2523, BL21 with or without the plasmid encoding rare tRNAs. The Rosetta 2 strain with pRARE from EMD Biosciences (Damstadt, Germany) was used as a control. After cultivation, the plasmid was then extracted and checked for resistance to StuIR digestion. The plasmids extracted from late-log phase (8 hours culture) showed little resistance to StuIR digestion, including the strain Rosetta 2. The plasmids from stationary phase (24 hours) were more resistant to StuIR digestion, achieving approximately 80% protection. The original pST2 was totally resistant to the StuIR digestion (>95% protection). There are a few possible reasons that may explain the experimental discrepancy: 1) unknown host mutations that facilitated stuIM gene expression; 2) prolonged culture of cells harboring pST2 plasmid under the conditions that cells stop replication, but methylase expression continues; and 3) small insignificant enhancement of stuIM gene expression by co-expression of rare tRNA.

The stuIM was amplified in PCR, digested with BamHI and SalI and cloned into low-copy-number plasmid pACYC184. Genomic DNA was prepared from cells harboring pACYC-stuIM and digested with StuIR. The genomic DNA was cleaved by StuIR. Therefore, pACYC-stuIM cannot be used for StuIR over-expression. Attempt was made to use non-cognate methylases to protect host DNA for StuIR expression.

(5) The Establishment of Pre-Modified *E. Coli* Strain for stuIM Expression

Since stuIM expressed from pACYC or pUC did not completely protect host DNA, other non-cognate methylases were tested for DNA modification. The recognition site of stuIM is AGGCCT. It is possible that those methylases that modify the internal sequence of the recognition site can modify the sequence and protect it from StuIR digestion. HaeIII methylase (GG$^{m5}$CC) Slatko et al. *Gene* 74:45-50 (1998)), FnuDI methylase (GGCC, modification site unknown, 5mC methylation type) and PhoI methylase (GGCC, modification site unknown, N4mC methylation type) genes were expressed in *E. coli*. The genomic DNAs were prepared from the following strains: ER1398 [pLJhaeIIIM101-1], ER1398 [pMMhaeII-IRM127-1, pACYC184fnuDIM] and ER2566 [pET21aphoIR & pLG339phoIM] and were digested with StuIR. The genomic DNAs from strains with haeIIIM or fnuDIM were resistant to stuIM digestion, and the DNA isolated from phoIM host was sensitive to StuIR digestion. ER2683 [pACYC-fnuDIM] was chosen to pre-modify the host DNA for expression of the putative stuIM gene.

(6) Expression of stuIR Gene in *E. coli*

The ORF adjacent to the stuIM gene was amplified in PCR, digested with HindIII and PstI and ligated to pUC19 with the compatible ends. The ligated plasmid was transformed into ER2683 pre-modified with pACYC-fnuDIM. Colonies were picked and grown in 4 ml of LB plus Amp and Cam overnight. Ten μl overnight cell culture from 38 samples was tested for StuIR activity on lambda DNA, 37° C., 30 min in NEB buffer 2 (Ipswich, Mass.). Sixteen out of 38 digested lambda DNA into completion, which confirmed the ORF to be the stuIR gene. Three clones (#6, #7 and #15) were sequenced using the primer from pUC19 vector. The inserts in #6 and #15 were confirmed to be the wild-type stuIR gene. The strain was then subjected to stability test in a large culture (10 ml cells passing from 1 L overnight culture to a fresh 1 L culture) and found to be stable. The plasmids were well maintained. The final expression yield of StuIR was found to be of $5 \times 10^6$ units per gram of wet cells.

With the amino acid sequence of StuIR identified, the database can be searched using the approach described in international application Pct/US06/30419 to identify related amino acid sequences corresponding to isoschizomers or neoschizomers of StuIR using an expectation value of less than E=e-02.

It should be noted that although the methylase and the restriction endonuclease were encoded by DNA on separate plasmids, it was possible to insert both genes on the same plasmid either under the same promoter e.g. lac promoter or different promoters e.g. tet promoter for the methylase and lac promoter for the restriction endonuclease.

The present invention is further illustrated by the following Examples. These Examples are provided to aid in the understanding of the invention and are not construed as a limitation thereof.

All references cited above and below are herein incorporated by reference.

EXAMPLE 1

Cloning of stuI R-M system in *E. coli*

1. Preparation of Genomic DNA

Genomic DNA was prepared from 15 g of *Streptomyces tubercidicus*, by the following steps:
 a. Resuspend 15 grams of cell paste in 35 ml of 0.1M Tris-HCl, 0.1M EDTA, pH 7.
 b. Add 25 ml of 2 mg/ml fresh lysozyme in 0.1M Tris-HCl, 0.1 MEDTA, pH7.6. Incubate at 37° C. for 1 hour.
 c. Add Pretease K to 0.1 mg/ml, 37° C. for 1 hour.
 d. Add SDS to 0.1% (6 ml of 10% stock).
 e. Add 6 ml of 8% sarcosyl solution.
 f. Freeze and thaw 3 times.
 g. Incubate at 55° C. for 1 hour.
 h. Phenol-CHCl$_3$ extraction 3 times, CHCl$_3$ extraction two times.
 i. Dialyze DNA in 4 L 10 mM Tris-HCl, pH7.5, 0.1 mM EDTA at 4° C., change buffer twice.
 j. Add 0.5 ml of RNaseA (1 mM) at 37° C. for 1 hour.
 k. Run 30 μl of DNA on 0.8% agarose gel. This procedure produced 640 μg genomic DNA. The size of the genomic DNA is much larger than 10 kb on gel.

2. Construction of the Plasmid pUC2iStuI

To construct the vector for the selection of possible methylase, two StuIR cleavage sites were incorporated into the bla (Amp-resistant) gene in pUC19 by two rounds of inverse PCR by the following primers.

```
Pair 1:
                                                   (SEQ ID NO:5)
5'-GCTTTTCTGTGACTGGTGAGGCCTCAACCAAGTCATTCTGAG-3'

(SEQ ID NO:6)
5'-CTCAGAATGACTTGGTTGAGGCCTCACCAGTCACAGAAAGC-3'

Pair 2:
                                                   (SEQ ID NO:7)
5'-CATTGGAAAACGTTCTTCAGGCCTAAACTCTCAAGGATCTTACC-3'

(SEQ ID NO:8)
5'-GGTAAGATCCTTGAGAGTTTTAGGCCTGAAGAACGTTTTCCAAT
G-3'
The StuIR cleavage site (AGGCCT) is underlined.
```

PCR was performed as the following: 0.25 μl pUC19 as PCR template in PCR 1 and 1 μl of pUC19 (StuI) as second round PCR template. Eighty pmol of primers, 400 μM dNTP, 4 units of Deep Vent™ polymerase (NEB, Ipswich, Mass.) in 1× Thermopol buffer (NEB, Ipswich, Mass.) with the addition of 0, 2 and 6 mM MgSO$_4$. The PCR condition is 94° C. 5 min, followed by 18 cycles of 95° C. 30 sec, 55° C. 30 sec and 72° C. 2 min and 42 sec and a final 2 min and 42 sec incubation.

The first pair of PCR primers introduced an Y103A mutation in the bla (Amp-resistant) gene, at the same time it eliminated the ScaI site. The second pair of PCR primer mutation is a silent mutation. The final vector can be digested by StuIR twice and the *E. coli* cells carrying the plasmid can be plated on normal Ampicilline plate (50 to 100 μg/ml). The plasmid was named pUC2iStuI (FIG. 4).

3. Restriction Digestion of Genomic DNA and Construction of Genomic DNA Library

Varying units of restriction enzymes ApoI (R/AATTY), NlaIII (/CATG), and Sau3AI (/GATC) were used to digest 4 μg genomic DNA to limited partial digestion. 0.5 μg digested DNA was analyzed on a 0.8% agarose gel. Only NlaIII and Sau3AI produced sufficient spectrum of the DNA fragments between 1.5 kb to 10 kb. The samples digested with same enzyme were pooled. The portion from 1.5 kb to 10 kb was gel-purified from a low-melting gel. The NlaIII and Sau3AI partially digested genomic DNA was ligated to SphI- and BamHI-digested pUC2iStuI, respectively. The ligated DNA was used to transform a DNAse I deficient host XL-10 (Stratagene, La Jolla, Calif.). Approximately 200,000 Amp$^R$ transformants were obtained from each library. The colonies were pooled together and plasmids were extracted. One µl of this mixed plasmid was transformed to Rosetta 2 strain from EMD Bioscience, Damstadt, Germany. The plasmids were extracted again to form the primary plasmid library.

4. Cloning stuIM Gene by the Methylase Selection Method

Different amounts of the primary plasmid DNA library (1 µl to 1/256 µl) were challenged with 200 units of StuI at 37° C. for 1 hour. The digested DNA was transformed into E. coli strain Rosetta 2, resulting in 6 AmpR survivors from the mixed libraries. Plasmid DNA from these survivors was prepared by the QIAprep Spin Miniprep Kit method, Qiagen, Valencia, Calif. The extracted plasmids were digested by StuIR. Five colonies (#1, #2, #4, #5, #6) were found to be resistant to StuIR digestion. #2 (pST2) was also resistant to ScaIR digestion. The other clones were false positives from contaminant DNA. To verify the pST2 plasmid really contained the desired sites, a PCR was performed with the two primers:

```
5'-GGCGCCTGATGCGGTATTTTC-3'    (SEQ ID NO:9)

5'-CACTCAAAGGCGGTAATACGG-3'    (SEQ ID NO:10)
```

Under the condition of 1 µl pST2 as template, 80 pmol primers, 4 units of Deep Vent™ polymerase, 400 µM dNTP each in 1× ThermoPol buffer (NEB, Ipswich, Mass.) at the condition of 94° C. 5 min followed by 25 cycles of 95° C. 30 sec, 55° C. 30 sec and 72° C. 2 min. The PCR product was a 2073 bp fragment. When pST2 and this PCR product were digested with StuIR, pST2 plasmid was resistant to StuIR digestion, while the PCR product was susceptible to StuIR digestion. This result confirmed that the pST2 contains the 2 StuI sites, which must be modified by stuIM and became resistant to StuIR digestion.

Three rounds of primer walking sequencing of the insert in the plasmid pST2 from both direction revealed an ORF of 1440 bp, encoding a protein of 479 amino acid. This ORF was homologous to N6A specific methylase. Other adjacent ORFs were homologous to a transcription factor or caax amino terminal protease family protein. The 1440 bp ORF was stuIM (FIG. 2).

5. Identification of stuIR

One µg each Streptomyces tubercidicus genomic DNA was digested with AgeI, AluI, BfaI, BglII, BsaAI, BsaBI, BsrFI, BstYI, EcoRI, HaeII, HhaI, HincII, HpyCH4V, KasI, NlaIV, NruI, TaqI and Tsp509I. All these enzymes were selected for the reason that they have one site near the upstream sequence of the stuIM. The digested DNA was self-ligated at 2 ng/µl concentration, with 200 units of T4 DNA ligase in 1× Quick Ligation buffer (NEB, Ipswich, Mass.). The ligated DNA was concentrated to 50 µl by spin column. 10 µl of each was used as the template for inverse PCR (IPCR). The following primers were used in inverse PCR:

```
5'-GATGGATGAGCCGGAAGTCCGGAT-3'    (SEQ ID NO:11)

5'-ACGACTCAAACTCCCAGGTGCCCA-3'    (SEQ ID NO:12)
```

The following PCR condition was employed: 10 µl template, 80 pmol primers, 400 µM dNTPs, 4 units of Deep Vent™ (exo⁻) in 1× ThermoPol 1× Thermopol buffer (NEB, Ipswich, Mass.). The reaction condition is 94° C. 5 min, followed by 30 cycles of 94° C. 30 sec, 65° C. 30 sec and 72° C. 2 min. The templates from BsrFI, EcoRI, HaeII, HpyCH4IV, KasI, NruI and Tsp509I produced PCR fragments that were purified. These PCR fragments were purified by spin column and sequenced by the inverse PCR primers.

The template from EcoRI digestion produced 983 bp of new sequence to the original template sequence. A complete ORF of 768 bp encoding a protein of 255 amino acid was identified. It is not homologous to any known genes in GenBank. It was the candidate gene for stuIR (FIG. 4).

6. Establishment of Pre-Modified E. Coli Strain for Expression of StuIR

The initial selection of the Rosetta 2 strain (EMD Bioscience, Damstadt, Germany) for the expression of the stuIM was due to the possibility of enhanced gene expression with supply of rare tRNAs. This strain carries a residual plasmid pRARE2. To investigate if this plasmid was necessary for the expression of the stuIM, pRARE2 was extracted and transformed into other E. coli strains: ER2502, ER2683, ER2566, ER2523, BL21. The plasmid pST2 was transformed into ER2502, ER2683, ER2566, ER2523, and BL21. Host strains with or without the resident plasmid pRARE2 were compared for StuIR cleavage site modification (Rosetta 2 strain used as a control). Surprisingly, only the original pST2 was totally resistant to StuIR digestion. The other strains including the newly transformed Rosetta 2 strain produced plasmids that were partially resistant to StuIR digestion. The pRARE2 plasmid did not seem to enhance the expression of the stuIM. The length of cell culture did play a significant role in StuIR cleavage site modification. It was found that >24 h incubation of cells in a shaker rendered plasmids more resistant to StuIR digestion. Plasmid carrying the stuIM gene isolated from a host cell ER2502 (without pRARE2) achieved approximately 80% resistance to StuIR digestion. Three possible reasons that may have contributed to the successful cloning of the stuIM gene: 1) the use of pRARE2 co-expression plasmid (this turned out not a critical step); 2) an unknown host cell mutation that facilitated stuIM gene expression; and 3) prolonged cell culture in stationary phase for cells carrying pST2.

The stuIM gene was amplified in PCR and cloned into pACYC184 by the following primers:

```
                                                 (SEQ ID NO:13)
5'-GGTGGTGGATCCGGAGGTAAATAAATGACGGTCGAAGTGCCGCAAC
GT-3'

(SEQ ID NO:14)
5'-GGTGGTGTCGACCTAGGTCAACCGACCCATCCGGAA-3'
```

The PCR was performed as the following conditions: 1 µl pST2, 80 pmol primers, 400 µM dNTPs, 4 units of Deep Vent™ in 1× ThermoPol buffer. The reaction condition was carried out at 94° C. 5 min followed by 25 cycyles of 94° C. 30 sec, 55° C. 30 sec and 72° C. 1 min 30 sec. The PCR product was then digested with BamHI and SalI, and ligated into pACYC184 with compatible ends. The ligated plasmid was transformed into ER2683 and plated on plate with Cam. Nineteen plasmids were analyzed for right size inserts. Six of them (#3, #4, #5, #9, #16 and #17) contained right size insert by BamHI and SalI digestion. However, when the genomic DNA from cells carrying the plasmid were tested against StuI digestion, none of them were resistant to StuIR digestion. It was concluded that pACYC-stuIM could not be used in the expression of StuIR.

Other non-cognate methylases were tested for the modification/protection of host DNA. The recognition site of StuIR is AGGCCT. It is possible that a non-cognate methylase that modifies the internal sequence can protect it from StuIR digestion. HaeIII methylase (GG$^{m5}$CC), FnuDI methylase (GGCC, modification site unknown, 5mC methylation type)

and PhoI methylase (GGCC, modification site unknown, N4mC methylation type) genes were expressed in *E. coli*. The genomic DNAs from different strains: ER1398 with pLJhaeIIIM101-1, ER1398 with pMMhaeIIIRM127-1 and pACYC184fnuDIM, and ER2566 with pET21aphoIR & pLG339phoIM were digested by StuIR. The genomic DNA from the strain with haeIIIM and fnuDIM was resistant to StuIR digestion while the one with phoIM was sensitive to StuIR digestion. Plasmid pACYC-fnuDIM was transferred into ER2683 to generate a pre-modified strain. The genomic DNA was again extracted and tested against StuIR digestion. It was resistant to StuIR digestion.

7. Over-Expression of StuIR in *E. Coli*.

The ORF adjacent to stuIM was amplified in PCR.

```
                                                    (SEQ ID NO:15)
5'-GGTGGTAAGCTTGGAGGTAAATAAATGTCAGTGAGTGCGGTCGAACA
GGT-3'

(SEQ ID NO:16)
5'-GGTGGTCTGCAGTCACAGCCGACCCCCTGCGAGG-3'
```

Figure 5:
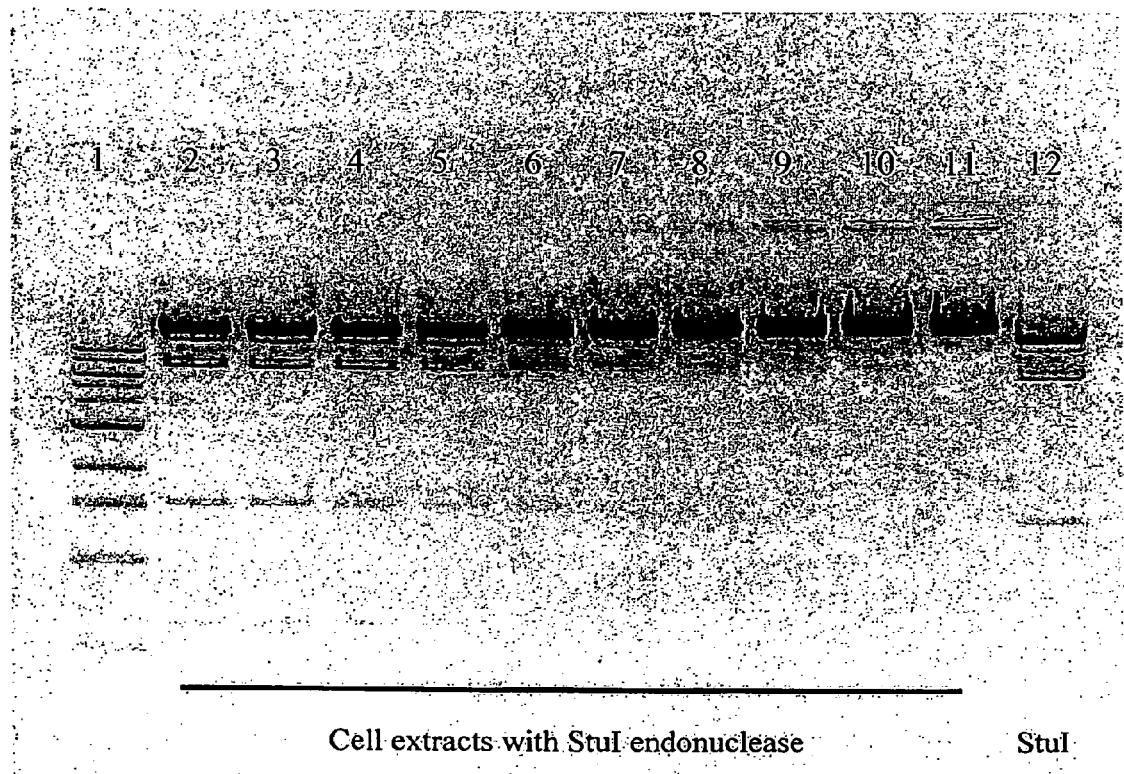
FIG. 5. Recombinant StuIR activity in cell extracts. Lambda DNA was used as the substrate. Lane 1, 1 kb DNA marker; Lanes 2-9, 3 µl 1/100, 1/200, 1/400, 1/800, 1/1600, 1/3200, 1/6400, 1/12800, 1/25600 diluted cell extracts added in the restriction digestions; Lane 12, Lambda DNA digested with native StuI.

PCR condition was as following: 10 µl *Streptomyces tubercidicus* genomic DNA, 80 pmol primers, 400 µM dNTP, 4 units of Deep Vent™ DNA polymerase in 1× ThermoPol buffer. The reaction condition was 94° C. for 5 min, 1 cycle; 95° C. for 30 sec, 55° C. for 30 sec, 72° C. for 46 sec for 25 cycles. The PCR product was digested by HindIII and PstI and ligated to pUC19 digested with same pair of enzymes. The ligated plasmid was transformed into ER2683 pre-modified with pACYC-fnuDIM. Transformants were plated on LB agar supplemented with Amp and Cam. Colonies were picked and grown in 4 ml LB with Amp and Cam overnight. Ten µl overnight cell culture from 38 samples was tested for StuIR activity on lambda DNA, 37° C., 30 min in NEB buffer 2. Sixteen out of 38 (#6, #7, #13, #15, #17, #18, #19, #20, #22, #23, #26, #27, #30, #34, #37 and #38) can digest the lambda DNA into complete pattern. The inserts in three clones (#6, #7 and #15) were sequenced using the primer from pUC19 vector (51233S and S1224S). The inserts in #6 and #15 were confirmed to be the wild-type stuIR. The strain was then subjected to stability test in a large culture by passing 10 ml of cells from 1 L overnight culture to a fresh 1 L culture. The StuIR expression strain was grown in 25 L culture in constitutive expression. After overnight culture, the final expression level of StuI was found to be ~5×10$^6$ units per gram of wet cells (FIG. 5).

EXAMPLE 2

A Method of Identifying Related Restriction Endonucleases Using the Amino Acid Sequence for StuIR The amino acid sequence of StuIR is used to perform a protein to protein (blastp) BLAST search, or a protein to translated database (tblastn) BLAST search. For example, such a search may be performed through the NCBI web server: www.ncbi.nlm.nih.gov/blast/ selectingthe blastp (or tblastn) program, and searching against the NR (non-redundant) database of "all organisms," using the standard preset values, which consist of Expect=10, word size=3, using the BLOSUM62 matrix and with gap costs of Existence=11, extension=1. These parameters can be varied by those skilled in the art to obtain slightly varied search results.

The output returned by the BLAST search is examined for sequences that give Expectation scores of less than e-02. These sequences are presumed to be REs.

The sequence context of the putative REs identified is examined to see if there is a putative DNA methyltransferase adjacent or near (within one or two ORFS) the putative endonuclease. The presence of such a methyltransferase is highly suggestive that the sequence identified using the known endonuclease sequence is an endonuclease.

The level of similarity between StuIR and the newly identified sequence can suggest whether the two sequences are isoschizomers (high degree of similarity, for example E<e-50) or may recognize related but different sequences (lesser degree of similarity).

The identified sequence is tested to see if it encodes a functional RE by any convenient methods of expressing protein from the sequence and testing that protein for endonucleolytic function, as described in FIG. 5. For example, the identified sequence may by amplified by PCR. The gene may then be expressed either in a cell-free in vitro transcription/translation system and the protein produced tested for endonuclease activity, or the gene may be introduced into a vector and cloned into a host cell, such as *E. coli*. The transformed host cells are then grown to allow the identified endonuclease gene to express protein, and a cell free lysate is prepared and tested for endonuclease activity.

What is claimed is:

1. An isolated DNA encoding a restriction endonuclease comprising SEQ ID NO: 2.

2. A recombinant vector comprising the isolated DNA according to claim 1.

3. A host cell transformed by a recombinant vector according to claim 2.

4. A method of producing an endonuclease, comprising: culturing a host cell transformed with a vector according to claim 2 under conditions suitable for expression of the endonuclease.

5. The isolated DNA of claim 1, wherein the restriction endonuclease cleaves DNA at the nucleotide sequence AGGCCT.

6. An isolated nucleic acid that encodes a polypeptide with at least 90% sequence identity to SEQ ID NO: 2.

7. A recombinant vector comprising the isolated nucleic acid according to claim 6.

8. A host cell transformed by a recombinant vector according to claim 7.

* * * * *

SEQUENCE LISTING

```
<160> NUMBER OF SEQ ID NOS: 16

<210> SEQ ID NO 1
<211> LENGTH: 768
<212> TYPE: DNA
<213> ORGANISM: unknown
<220> FEATURE:
<223> OTHER INFORMATION: StuI restriction endonuclease gene

<400> SEQUENCE: 1
gtgtcagtga gtgcggtcga acaggtattt ttggaatgcg agcgcgctcg ggcagacggt      60
gacttgattc agcgggtctc cgccagtgat aaggagtacc actttcagaa ttgggtgcag     120
gcccgcatag aggcatgcag gctttcgtac gatgatcctg gccggaacac ctatccggac     180
ttccggctca tccatcaccc ggaagggtat gaggtcaagg gcctggagtt tcccggccgc     240
```

```
gaggcggact acgactcaaa ctcccaggtg cccaccggta accacggcgg ccgtgaggtc    300
ttctacgtgt tcggtcgcta cccgaaggca gagcgcggcg tcgatgagta tccagttgta    360
gatctggtgg tgtgccacgg cagcttcctc aatgccgata gtgagtacgt tcataagaac    420
aagtcgttcc gtggctttgg ctcgtacgga gacatcctgg tccgcgaccg caaaatgtac    480
gtcgtgccaa cgccgttcgc actagcttcc ggaaccgcag ggctcgcgac cctgatcgtg    540
cctactgaat tcgagccaca gtcggatact ctcgttcagg tgggtgaact tgatcggacc    600
gaggttgacg aggtcatcgt gtcgtacgag ttcaaccttc agacaaatga gatggtgacg    660
cataaggcgc cgaatctcaa tgcaggtaag gtccacagtt ccgagcata tcgctcgcgc    720 ggtgcgggcg attctaagcc ggtttccctc gcaggggtc ggctgtga                  768
```

<210> SEQ ID NO 2
<211> LENGTH: 255
<212> TYPE: PRT
<213> ORGANISM: unknown
<220> FEATURE:
<223> OTHER INFORMATION: encoded amino acid for StuI restriction
      endonuclease

<400> SEQUENCE: 2

```
Met Ser Val Ser Ala Val Glu Gln Val Phe Leu Glu Cys Glu Arg Ala
1               5                   10                  15

Arg Ala Asp Gly Asp Leu Ile Gln Arg Val Ser Ala Ser Asp Lys Glu
            20                  25                  30

Tyr His Phe Gln Asn Trp Val Gln Ala Arg Ile Glu Ala Cys Arg Leu
        35                  40                  45

Ser Tyr Asp Asp Pro Gly Arg Asn Thr Tyr Pro Asp Phe Arg Leu Ile
    50                  55                  60

His His Pro Glu Gly Tyr Glu Val Lys Gly Leu Glu Phe Pro Gly Arg
65                  70                  75                  80

Glu Ala Asp Tyr Asp Ser Asn Ser Gln Val Pro Thr Gly Asn His Gly
                85                  90                  95

Gly Arg Glu Val Phe Tyr Val Phe Gly Arg Tyr Pro Lys Ala Glu Arg
            100                 105                 110

Gly Val Asp Glu Tyr Pro Val Val Asp Leu Val Val Cys His Gly Ser
        115                 120                 125

Phe Leu Asn Ala Asp Ser Glu Tyr Val His Lys Asn Lys Ser Phe Arg
    130                 135                 140

Gly Phe Gly Ser Tyr Gly Asp Ile Leu Val Arg Asp Arg Lys Met Tyr
145                 150                 155                 160

Val Val Pro Thr Pro Phe Ala Leu Ala Ser Gly Thr Ala Gly Leu Ala
                165                 170                 175

Thr Leu Ile Val Pro Thr Glu Phe Glu Pro Gln Ser Asp Thr Leu Val
            180                 185                 190

Gln Val Gly Glu Leu Asp Arg Thr Glu Val Asp Glu Val Ile Val Ser
        195                 200                 205

Tyr Glu Phe Asn Leu Gln Thr Asn Glu Met Val Thr His Lys Ala Pro
    210                 215                 220

Asn Leu Asn Ala Gly Lys Val His Ser Phe Arg Ala Tyr Arg Ser Arg
225                 230                 235                 240

Gly Ala Gly Asp Ser Lys Pro Val Ser Leu Ala Gly Gly Arg Leu
                245                 250                 255
```

<210> SEQ ID NO 3
<211> LENGTH: 1440

```
<212> TYPE: DNA
<213> ORGANISM: unknown
<220> FEATURE:
<223> OTHER INFORMATION: StuI methylase gene

<400> SEQUENCE: 3
gtgacggtcg aagtgccgca acgtaccagc ctggagtcaa actttccggc agcgatgctt      60
agtggcgtcg gcacgaagga atcctggcgc aaggaagtcc accgcccagc caccagcacg     120
cacaagtggt gggcgaagcg cctcggcacc gtatttcggg ggatcattac gtcggcgacg     180
acgcccgatg gagccgatgc tgtgggagcc tacggatcgt cgctcgatct ggcgggagcc     240
attgtgctcg acccgttctc tggctcgggt gtgaccggcg tggaagccct caaactcggg     300
gctaaggctg tttgtttcga catcaaccct gtggcaacgc tcgttcagcg tcaagctgtt     360
caaccgtggg acctcgggtc tcttgaagct gcctacaaag aggtcgagtc ggcctgtcgg     420
tcagaggttg atcgactcca ccgtacagag gacgggagga ctgttctcta ctacttctgg     480
gtcgcgaccc tcgggtgccc cgagtgctcc aaagaagttc gcttgttcga ctcgccagtg     540
ttctctaaga acgcttaccc gaagcgagta cccaaagccc aaattgtctg tcccgagtgc     600
ctctccgtta aggagagtcg gtatgacttc gtcacggaga cgtgtttgaa gggccacgtc     660
attacgcagc gcggtgcagc gcggggtcag ttggcgacat gcgggaacgg tcacagcttc     720
aaggtcctcg gcgccctgaa cgggtcgcca ccggtatacg agatgtatgc caagatggtg     780
gccaactcgg acgggtcgaa gagctacgaa gccatcaccg actgggacag ggaactctac     840
gacgagtgcg ttgcagcgct cgcagggcta tcgcagtctg ccgtgcttcc acgcggtcgg     900
cttgctcccg gcaataatac tgaccaggct ctgaagtgga attttcggga atggcgcgaa     960
ttcttcaacg cgcgccagct ggtttccctc tcgctgatgg cgacggcgat ccgtgacctg    1020
actggatcgc ctgaacgcga agcgctttgt gccctgtttt caggaacgct tgagttcaat    1080
aacctgttca catcgttcaa aggcgagggg acggggctg tccggcatat gttcagtcat    1140
cacatcctca cgccggagcg gactccactg gaggcgcacc cctggggacg tcgcagtcct    1200
ccggtgcgtt ctccactctc ttcaagagtc gtctgcagcg tgctcacgag tacaagacga    1260
aacctgcaga cctcgttgac cggggtgcag ggatcgagcg gatctccgga gtgtcaaagc    1320
cagtgggcgc gagcattgcg gactcatggg agtctttcgt ctcgatcgaa gggcaggcgg    1380
cctatgtcgc caccagaaac tcggcacaga cggatattcc ggatgggtcg gttgacctag    1440

<210> SEQ ID NO 4
<211> LENGTH: 479
<212> TYPE: PRT
<213> ORGANISM: unknown
<220> FEATURE:
<223> OTHER INFORMATION: encoded amino acid for StuI methylase gene

<400> SEQUENCE: 4

Met Thr Val Glu Val Pro Gln Arg Thr Ser Leu Glu Ser Asn Phe Pro
1               5                  10                  15

Ala Ala Met Leu Ser Gly Val Gly Thr Lys Glu Ser Trp Arg Lys Glu
            20                  25                  30

Val His Arg Pro Ala Thr Ser Thr His Lys Trp Trp Ala Lys Arg Leu
        35                  40                  45

Gly Thr Val Phe Arg Gly Ile Ile Thr Ser Ala Thr Thr Pro Asp Gly
    50                  55                  60

Ala Asp Ala Val Gly Ala Tyr Gly Ser Ser Leu Asp Leu Ala Gly Ala
65                  70                  75                  80
```

```
Ile Val Leu Asp Pro Phe Ser Gly Gly Val Thr Gly Val Glu Ala
             85                  90                  95

Leu Lys Leu Gly Ala Lys Ala Val Cys Phe Asp Ile Asn Pro Val Ala
            100                 105                 110

Thr Leu Val Gln Arg Gln Ala Val Gln Pro Trp Asp Leu Gly Ser Leu
            115                 120                 125

Glu Ala Ala Tyr Lys Glu Val Glu Ser Ala Cys Arg Ser Glu Val Asp
            130                 135                 140

Arg Leu His Arg Thr Glu Asp Gly Arg Thr Val Leu Tyr Tyr Phe Trp
145                 150                 155                 160

Val Ala Thr Leu Gly Cys Pro Glu Cys Ser Lys Glu Val Arg Leu Phe
                165                 170                 175

Asp Ser Pro Val Phe Ser Lys Asn Ala Tyr Pro Lys Arg Val Pro Lys
            180                 185                 190

Ala Gln Ile Val Cys Pro Glu Cys Leu Ser Val Lys Glu Ser Arg Tyr
            195                 200                 205

Asp Phe Val Thr Glu Thr Cys Leu Lys Gly His Val Ile Thr Gln Arg
            210                 215                 220

Gly Ala Ala Arg Gly Gln Leu Ala Thr Cys Gly Asn Gly His Ser Phe
225                 230                 235                 240

Lys Val Leu Gly Ala Leu Asn Gly Ser Pro Pro Val Tyr Glu Met Tyr
                245                 250                 255

Ala Lys Met Val Ala Asn Ser Asp Gly Ser Lys Ser Tyr Glu Ala Ile
            260                 265                 270

Thr Asp Trp Asp Arg Glu Leu Tyr Asp Glu Cys Val Ala Ala Leu Ala
            275                 280                 285

Gly Leu Ser Gln Ser Ala Val Leu Pro Arg Gly Arg Leu Ala Pro Gly
            290                 295                 300

Asn Asn Thr Asp Gln Ala Leu Lys Trp Asn Phe Arg Glu Trp Arg Glu
305                 310                 315                 320

Phe Phe Asn Ala Arg Gln Leu Val Ser Leu Ser Leu Met Ala Thr Ala
                325                 330                 335

Ile Arg Asp Leu Thr Gly Ser Pro Glu Arg Glu Ala Leu Cys Ala Leu
            340                 345                 350

Phe Ser Gly Thr Leu Glu Phe Asn Asn Leu Phe Thr Ser Phe Lys Gly
            355                 360                 365

Glu Gly Thr Gly Ala Val Arg His Met Phe Ser His Ile Leu Thr
            370                 375                 380

Pro Glu Arg Thr Pro Leu Glu Ala His Pro Trp Gly Arg Arg Ser Pro
385                 390                 395                 400

Pro Val Arg Ser Pro Leu Ser Ser Arg Val Val Cys Ser Val Leu Thr
                405                 410                 415

Ser Thr Arg Arg Asn Leu Gln Thr Ser Leu Thr Gly Val Gln Gly Ser
            420                 425                 430

Ser Gly Ser Pro Glu Cys Gln Ser Gln Trp Ala Arg Ala Leu Arg Thr
            435                 440                 445

His Gly Ser Leu Ser Ser Arg Ser Lys Gly Arg Pro Met Ser Pro
450                 455                 460

Pro Glu Thr Arg His Arg Arg Ile Phe Arg Met Gly Arg Leu Thr
465                 470                 475

<210> SEQ ID NO 5
<211> LENGTH: 42
<212> TYPE: DNA
<213> ORGANISM: unknown
```

```
<220> FEATURE:
<223> OTHER INFORMATION: primer

<400> SEQUENCE: 5
gcttttctgt gactggtgag gcctcaacca agtcattctg ag                    42

<210> SEQ ID NO 6
<211> LENGTH: 41
<212> TYPE: DNA
<213> ORGANISM: unknown
<220> FEATURE:
<223> OTHER INFORMATION: primer

<400> SEQUENCE: 6
ctcagaatga cttggttgag gcctcaccag tcacagaaag c                     41

<210> SEQ ID NO 7
<211> LENGTH: 44
<212> TYPE: DNA
<213> ORGANISM: unknown
<220> FEATURE:
<223> OTHER INFORMATION: primer

<400> SEQUENCE: 7
cattggaaaa cgttcttcag gcctaaactc tcaaggatct tacc                  44

<210> SEQ ID NO 8
<211> LENGTH: 45
<212> TYPE: DNA
<213> ORGANISM: unknown
<220> FEATURE:
<223> OTHER INFORMATION: primer

<400> SEQUENCE: 8
ggtaagatcc ttgagagttt taggcctgaa gaacgttttc caatg                 45

<210> SEQ ID NO 9
<211> LENGTH: 21
<212> TYPE: DNA
<213> ORGANISM: unknown
<220> FEATURE:
<223> OTHER INFORMATION: primer

<400> SEQUENCE: 9
ggcgcctgat gcggtatttt c                                           21

<210> SEQ ID NO 10
<211> LENGTH: 21
<212> TYPE: DNA
<213> ORGANISM: unknown
<220> FEATURE:
<223> OTHER INFORMATION: primer

<400> SEQUENCE: 10
cactcaaagg cggtaatacg g                                           21

<210> SEQ ID NO 11
<211> LENGTH: 24
<212> TYPE: DNA
<213> ORGANISM: unknown
<220> FEATURE:
<223> OTHER INFORMATION: primer

<400> SEQUENCE: 11
gatggatgag ccggaagtcc ggat                                        24
```

```
<210> SEQ ID NO 12
<211> LENGTH: 24
<212> TYPE: DNA
<213> ORGANISM: unknown
<220> FEATURE:
<223> OTHER INFORMATION: primer

<400> SEQUENCE: 12
acgactcaaa ctcccaggtg ccca                                          24

<210> SEQ ID NO 13
<211> LENGTH: 48
<212> TYPE: DNA
<213> ORGANISM: unknown
<220> FEATURE:
<223> OTHER INFORMATION: primer

<400> SEQUENCE: 13
ggtggtggat ccggaggtaa ataaatgacg gtcgaagtgc cgcaacgt                48

<210> SEQ ID NO 14
<211> LENGTH: 36
<212> TYPE: DNA
<213> ORGANISM: unknown
<220> FEATURE:
<223> OTHER INFORMATION: primer

<400> SEQUENCE: 14
ggtggtgtcg acctaggtca accgacccat ccggaa                             36

<210> SEQ ID NO 15
<211> LENGTH: 50
<212> TYPE: DNA
<213> ORGANISM: unknown
<220> FEATURE:
<223> OTHER INFORMATION: primer

<400> SEQUENCE: 15
ggtggtaagc ttggaggtaa ataaatgtca gtgagtgcgg tcgaacaggt              50

<210> SEQ ID NO 16
<211> LENGTH: 34
<212> TYPE: DNA
<213> ORGANISM: unknown
<220> FEATURE:
<223> OTHER INFORMATION: primer

<400> SEQUENCE: 16
ggtggtctgc agtcacagcc gaccccctgc gagg                               34
```